United States Patent
Wang et al.

(10) Patent No.: US 10,402,992 B2
(45) Date of Patent: Sep. 3, 2019

(54) METHOD AND APPARATUS FOR ENDOSCOPE WITH DISTANCE MEASURING FOR OBJECT SCALING

(71) Applicant: CAPSOVISION, INC., Saratoga, CA (US)

(72) Inventors: Kang-Huai Wang, Saratoga, CA (US); Chenyu Wu, Sunnyvale, CA (US); Yi Xu, Menlo Park, CA (US)

(73) Assignee: CapsoVision Inc., Saratoga, CA (US)

( * ) Notice: Subject to any disclaimer, the term of this patent is extended or adjusted under 35 U.S.C. 154(b) by 0 days.

(21) Appl. No.: 15/883,337

(22) Filed: Jan. 30, 2018

(65) Prior Publication Data

US 2018/0174318 A1 Jun. 21, 2018

Related U.S. Application Data

(63) Continuation of application No. PCT/US2017/015668, filed on Jan. 30, 2017, and a
(Continued)

(51) Int. Cl.
*A61B 1/04* (2006.01)
*G06T 7/521* (2017.01)
(Continued)

(52) U.S. Cl.
CPC .......... *G06T 7/521* (2017.01); *A61B 1/00009* (2013.01); *A61B 1/041* (2013.01);
(Continued)

(58) Field of Classification Search
CPC . G06T 7/521; G06T 7/62; G06T 2207/10152; G06T 2207/10068;
(Continued)

(56) References Cited

U.S. PATENT DOCUMENTS 6,469,289 B1   10/2002   Scott-Thomas
6,977,685 B1   12/2005   Acosta-Serafini et al.
(Continued)

OTHER PUBLICATIONS

Rasouli et al, Wireless capsule endoscope for enhanced diagnostic inspection of gastrointestinal tract (Year: 2010).*
(Continued)

*Primary Examiner* — Shan E Elahi
(74) *Attorney, Agent, or Firm* — Blairtech Solution LLC

(57) ABSTRACT

A method and apparatus for capturing images of a scene using a capsule device including a camera are disclosed. An image sequence is captured using the camera when the capsule device travels through a human gastrointestinal tract. Also, structured-light images are captured using the camera by projecting structured light to one or more objects in a field of view of the camera when the capsule device travels through the human gastrointestinal tract. The structured-light images are interleaved with regular images in the image sequence. The distance information with respect to the capsule camera associated with objects of the selected image is derived. Both the image sequence and the distance information are outputted. A method of determining the size of an object of interest utilizing the distance information is also disclosed. In another method, the distance information is used to scale object or adjust intensities.

20 Claims, 4 Drawing Sheets

Related U.S. Application Data continuation-in-part of application No. 14/884,788, filed on Oct. 16, 2015, now Pat. No. 9,936,151.

(51) Int. Cl.
| | |
|---|---|
| *G06T 7/62* | (2017.01) |
| *H04N 5/225* | (2006.01) |
| *H04N 5/222* | (2006.01) |
| *A61B 1/00* | (2006.01) |
| *A61B 5/107* | (2006.01) |
| *A61B 5/07* | (2006.01) |
| *A61B 1/06* | (2006.01) |

(52) U.S. Cl.
CPC ............ *A61B 5/073* (2013.01); *A61B 5/1076* (2013.01); *G06T 7/62* (2017.01); *H04N 5/2226* (2013.01); *H04N 5/2256* (2013.01); *A61B 1/0661* (2013.01); *G06T 2207/10028* (2013.01); *G06T 2207/10068* (2013.01); *G06T 2207/10152* (2013.01); *G06T 2207/30028* (2013.01); *H04N 2005/2255* (2013.01)

(58) Field of Classification Search
CPC . G06T 2207/30028; G06T 2207/10028; A61B 5/1076; A61B 1/00009; A61B 1/0661; A61B 1/041; H04N 5/2226; H04N 5/2256; H04N 2005/2255
USPC .......................................................... 348/65
See application file for complete search history.

(56) References Cited

U.S. PATENT DOCUMENTS

| | | | | |
|---|---|---|---|---|
| 7,433,133 | B2* | 10/2008 | Kislev | A61B 1/00096 348/65 |
| 7,577,283 | B2* | 8/2009 | Zinaty | A61B 1/041 348/45 |
| 7,983,458 | B2 | 7/2011 | Wang | |
| 8,044,996 | B2* | 10/2011 | Rice | A61B 5/0059 348/50 |
| 2004/0171914 | A1* | 9/2004 | Avni | A61B 1/041 600/160 |
| 2006/0113459 | A1 | 6/2006 | Yang et al. | |
| 2006/0268153 | A1* | 11/2006 | Rice | A61B 5/0059 348/370 |
| 2009/0259102 | A1* | 10/2009 | Koninckx | A61B 1/00181 600/111 |
| 2012/0188560 | A1 | 7/2012 | Bendall et al. | |
| 2014/0046408 | A1* | 2/2014 | Shoham | A61N 5/0601 607/88 |
| 2014/0098224 | A1 | 4/2014 | Zhang | |
| 2014/0249373 | A1* | 9/2014 | Arneson | A61B 1/00041 600/160 |
| 2014/0316265 | A1* | 10/2014 | Levin | A61B 1/31 600/434 |

OTHER PUBLICATIONS

Jin et al, Broadband hybrid water antenana for ISM-band ingestible capsule endoscope systems (Year: 2016).*

* cited by examiner

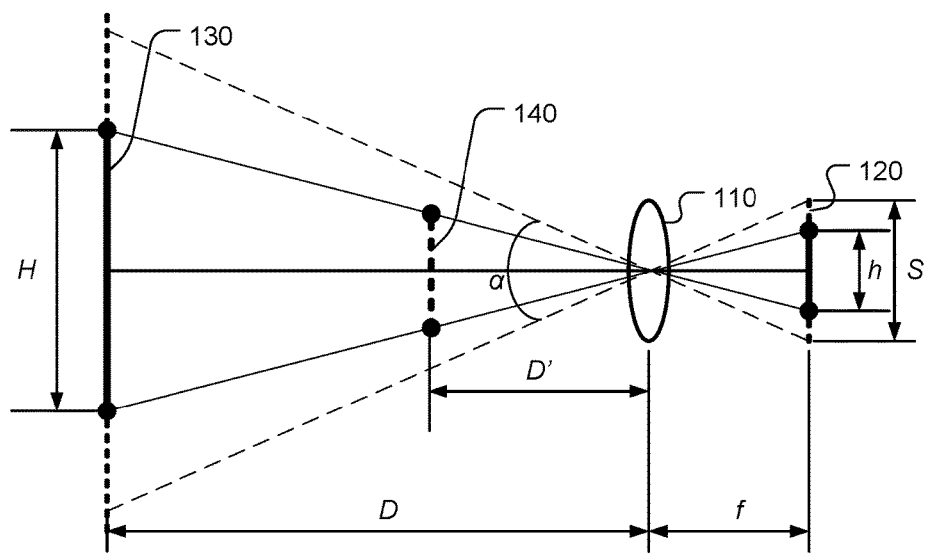
Fig. 1
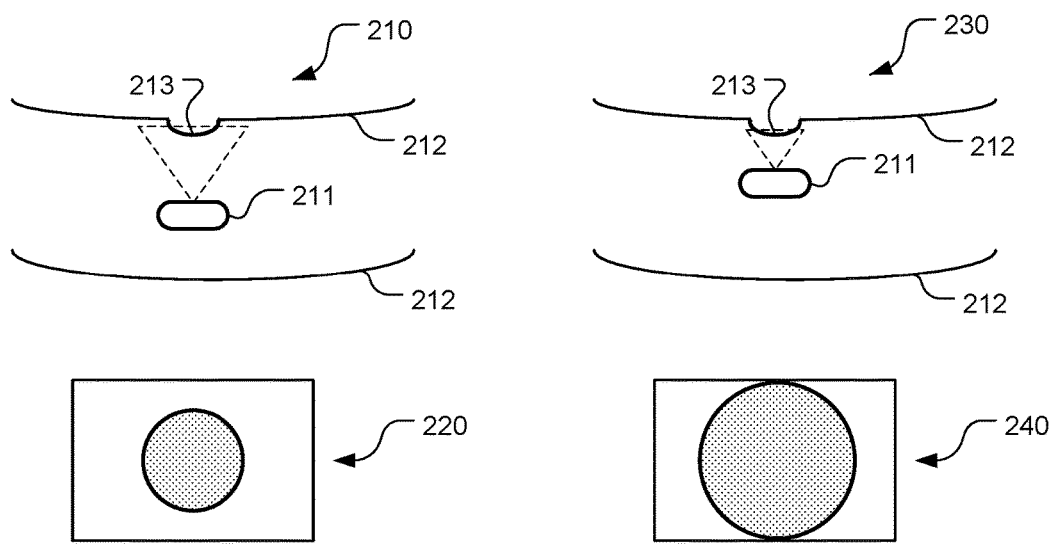
Fig. 2A  Fig. 2B

METHOD AND APPARATUS FOR ENDOSCOPE WITH DISTANCE MEASURING FOR OBJECT SCALING

CROSS REFERENCE TO RELATED APPLICATIONS

The present invention is a continuation application of and claims priority to PCT Patent Application Serial No. PCT/US17/15668, filed on Jan. 30, 2017. The present invention is also a continuation-in-part application and claims priority to U.S. patent application Ser. No. 14/884,788, filed on Oct. 16, 2015. The present invention is also related to U.S. Pat. No. 7,983,458, granted on Jul. 19, 2011. The PCT Patent Application, U.S. Patent and U.S. Patent Application are hereby incorporated by reference in their entireties.

FIELD OF THE INVENTION

The present invention relates to the endoscope for capturing images of human gastrointestinal (GI) tract for diagnosis purpose. In particular, the endoscope is enabled to measure distance of objects in the field of view of the camera. The distance information can be used subsequently to process the image sequence captured, such as measuring a size of an object of interest or stitching the image sequence to reduce viewing time.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools.

Capsule endoscope is an alternative in vivo endoscope developed in recent years. For capsule endoscope, a camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. The capsule camera with on-board storage archives the captured images in on-board non-volatile memory. The capsule camera is retrieved upon its exiting from the human body. The images stored in the non-volatile memory of the retrieved capsule camera are then accessed through an output port on in the capsule camera.

When the endoscope is used for imaging the human GI tract, one of the primary purposes is to identify any possible anomaly. If any anomaly is found, it is further of interest to determine characteristics of the anomaly, such as the size of the anomaly. The captured images will be examined by medical profession for examination or diagnosis. The number of images captured is typically 25,000 or more. It will require a long reviewing time to look through the images even by skilled professionals. Accordingly, image stitching has been used to reduce the number of images to be viewed. For example, in PCT Patent Application Publication, Serial No. WO2014/193670 A2, published on Dec. 4, 2014, image stitching for images captured using a capsule camera is disclosed. It is desirable to develop methods or apparatus that are capable to further improve the efficiency of image stitching.

BRIEF SUMMARY OF THE INVENTION

A method and apparatus for capturing images of a scene using a capsule camera are disclosed. After the capsule camera is swallowed by a patient, an image sequence is captured using the capsule camera when the capsule camera travels through the human gastrointestinal tract. Also, structured-light images are captured when the capsule camera travels through the human gastrointestinal tract. Both the regular images and the structured-light images or derived information of the structured-light images are outputted. The distance information associated with objects of the regular images with respect to the capsule camera can be derived.

The association information between the distance information and corresponding images of the regular images is outputted. The association information may correspond to frame numbers or capture times of the corresponding images of the regular images.

The present invention also discloses a method of determining the size of an object of interest in an image. The regular images captured by a capsule camera along with the structured-light images are received. The distance information associated with the objects in the regular images with respect to the camera is derived from the structured-light images. The size of an object of interest in a selected regular image can be determined based on the pixel data of the target object and the distance information. The size of the object of interest is determined according to the image size of the object of interest in a selected regular image scaled by a ratio of object distance to the capsule camera and focal length of the capsule camera. The image size of the object of interest in the selected regular image can be measured in terms of a number of pixels of object of interest in the selected regular image.

The present invention further discloses a method of stitching the regular images utilizing information including the distance information to generate a stitched image sequence. Again, the distance information can be derived from the structured-light images. In one embodiment, the distance information is used to scale the objects of the regular images for stitching the regular images. In another embodiment, the distance information is used to adjust image intensities of the regular images for stitching the image sequence.

BRIEF DESCRIPTION OF THE DRAWINGS

FIG. 1 illustrates an example of relationship among the size of an object, the size of the corresponding object image, the object distance and the focal length of the camera.

FIG. 2A and FIG. 2B illustrate an example of the different sizes of object images for a same object in two images captured at two different object distances.

DETAILED DESCRIPTION OF THE INVENTION

Figure 3:
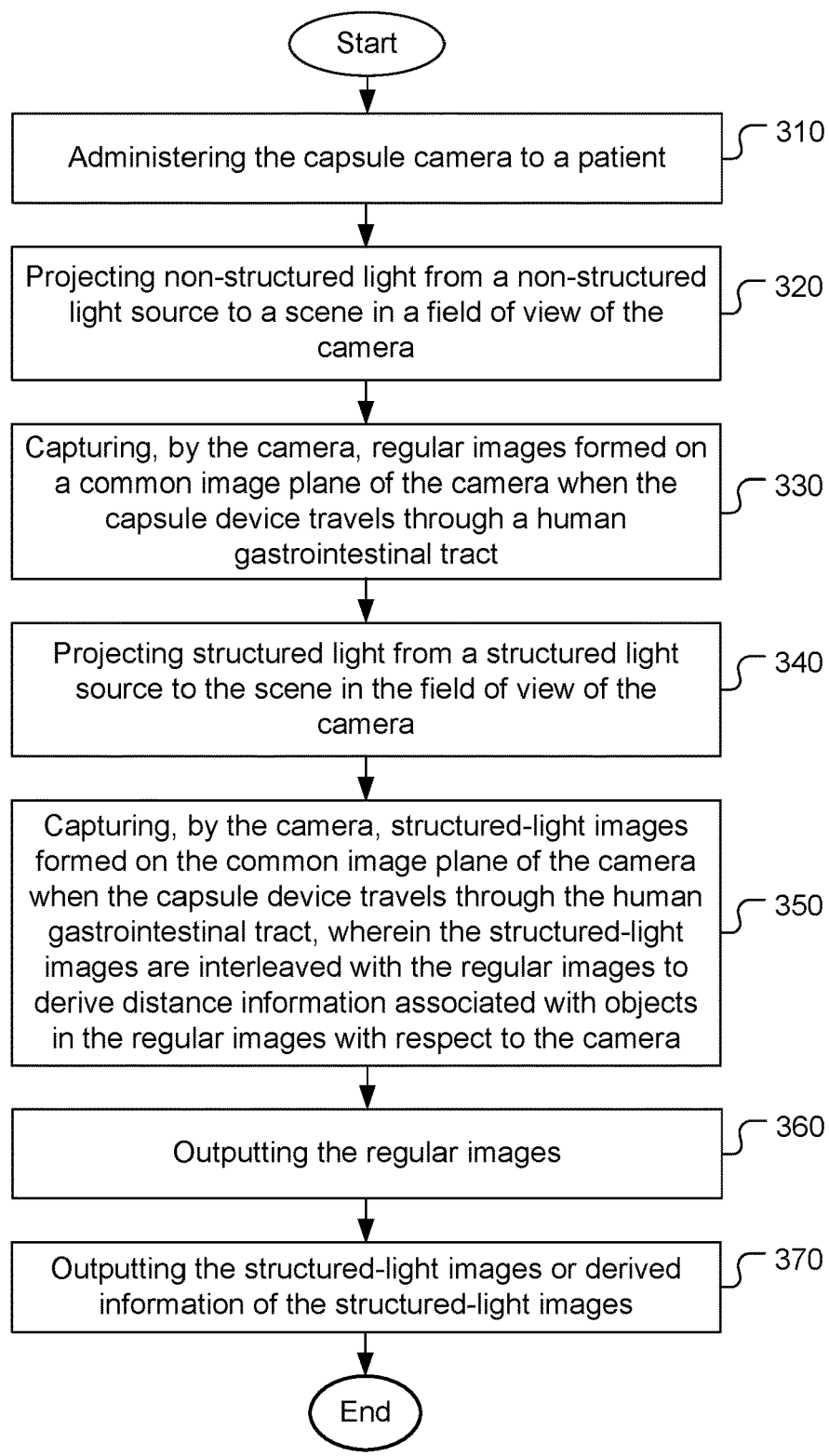
FIG. 3 illustrates an exemplary flowchart for capturing regular images along with structured-light images according to an embodiment of the present invention, where the structured-light images are used to derive distance information associated with objects in the regular images with respect to the camera.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, components, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Endoscopes are normally inserted into the human body through a natural opening such as the mouth or anus. Therefore, endoscopes are preferred to be small sizes so as to be minimally invasive. As mentioned before, endoscopes can be used for diagnosis of human gastrointestinal (GI) tract. The captured image sequence can be viewed to identify any possible anomaly. If any anomaly is found, it is of interest to identify the characteristics of the anomaly, such as the size. Accordingly, an invention of the present invention discloses an endoscope including a distance measuring means to measure the object distances between the camera and various locations of an object in the field of view of the camera.

There are various known means for measuring the distance between the camera and various locations of an object in the field of view of the camera. For example, there is a class of distance measuring devices that determine the distance based on ToF (Time of Flight) or phase shift of a light source. The light source may be a laser or LED (Light Emitting Diode). A light sensor is used to detect the returned light. The time difference or phase difference between the emitted light from the light source and the received light by the light detector is used to determine the distance. Ultrasonic wave is also a signal source that can be used to measure the distance between an object and the camera for the intended GI imaging application. The distance measuring means is well-known in the field and various literatures describing the distance measure based on ToF or phase shift using light or ultrasound sources are readily available. Therefore, details for distance measuring means based on ToF or phase shift using light or ultrasound sources are omitted in this disclosure.

If a light source is used to measure the distance, the light for measuring the distance may interfere with the flash light illuminating the GI tract during image capture. In this case, the light for distance measuring and the flash light for image capture will not be applied at the same time, or at least one of the light sources needs to be substantially dimmed. The distance information can be stored separately or stored with an associated image. The distance information can be captured before or after an associated image. If the distance information is stored separately, the related information (named as association information in this disclosure) for the associated image will also be stored so that the distance information can be properly used. The related information can be capture time, frame time or frame number of the associated image. If the ultrasound is used to measure the distance, the distance measuring using ultrasound and image capturing by applying the flash light to illuminating the GI tract may occur at the same time.

While the distance measuring means based on ToF or phase shift using light or ultrasound is well known, to fit such distance measuring means into an endoscope is a challenging task and costly with larger size not suitable for endoscope application. Accordingly, other distance measuring means are based on image processing of images captured using an image sensor.

For example, one technique for capturing depth information is to use a color filter placed on top of selected sensor pixels with the passband reasonably narrow and capture the color information and depth information simultaneously. The environment light sources with spectrum in the filter passband will cause negligible amount of energy projected onto the sensor. For the case of RGB pixels, a fourth type of pixels may be added to capture light with the spectrum in the passband of the filter placed on top of these pixels. Then, the structured light that has the spectrum substantially in the passband can be projected onto the scene. However this approach will reduce the spatial resolution of the images or video captured using such image sensor and require the use of an unconventional color filter.

Another technique is to obtain the depth information as well as 3D topology by projecting structured-light patterns that are visible in the RGB sensors. However the real time image and/or video will be confounded by the structured light superimposed on it. When a structured image is captured, the depth or shape information for objects in the scene is derived. The depth or shape information is then assumed by the image or images captured shortly before or after the structured light image. Since the regular images are captured by a capsule endoscope at a relatively slow frame rate (e.g. 5 frames per second), the scene corresponds to the image captured using the structured light and the scene corresponds to a regular image may be noticeably different due to the endoscope movement or the peristaltic motion of the intestines. In order to improve the accuracy of the derived depth information from the structured light images, the structured images with shortened frame period is disclosed in U.S. patent application Ser. No. 14/884,788, filed on Oct. 16, 2015. Since the structured light image is closer in time with the corresponding regular image, the depth information derived should be more accurate than that derived based on a structured-light image with a longer frame period.

When the distance measuring means via structured light is used, the depth (i.e., distance) information will be derived from the structured-light images. In other words, the raw distance information is stored in the form of structured-light images. In this case, the distance information (i.e., the structured-light images) can be stored separately or stored with an associated image taken under regular light. The distance information can be captured before or after an associated image. If the distance information is stored separately, the related information (i.e., association information) for the associated image will also be stored so that the distance information can be properly used. Techniques to derive the depth information from the structured-light images are known in the field. Details of the depth derivation from the structured-light images are omitted in this disclosure.

In an endoscope, the focal length is known by design. If the distance (also named as object distance in this disclosure) between an object and the camera can be determined, the dimensions of an object can be determined simply using geometry. FIG. 1 illustrates a simplified example of object dimension determination based on object-camera distance. In a camera system, the image sensor is placed at the focal plane 120 behind the lens 110. The camera can capture a scene within the field of view extending an angle α. The focal length f is the distance between the lens and the image sensor. The focal length often is fixed for endoscopic applications and is known by design. However, when a capsule endoscope travels through the GI tract, the object distance D varies depending on the location of the capsule endoscope and its relative angles with respect to the GI wall being imaged. If the distance D is known, the dimension of an object can be determined from the captured image by measuring the size of the object image in the image. For example, if an object 130 with height H is at distance D from the camera, the object image height H can be derived from the object image height h in the image according to:

$$H = \frac{h}{f} D. \quad (1)$$

In the above equation, h is measured from the image, the focal length f is known by design, and the distance D is determined by a selected distance measuring means as mentioned above. Accordingly, if the distance can be determined, the object dimensions can be derived. The object size in the image can be measured in physical dimension. However, the image is captured digitally and the size measurement may be more convenient in terms of the number of pixels. Since the physical dimension of image sensor surface and the optical footprint are known. Also, the number of pixels is known (e.g. 320×240). Therefore, the object image size in the image can be measured in a number of pixels and converted physical object image size in the image.

As shown above, the object image size in the image depends on the actual object size and its distance from the camera. A smaller object at a closer distance may appear to have the same size in the image as a larger object at a farther distance. For example, the object 140, which is smaller but closer than object 130, appears to have the same height as object 130 in the image. Therefore, the distance is crucial information for determining the object size. Accordingly, the distance measuring means disclosed above enables object size determination based on the images captured using an endoscope.

Distance information is also useful for image stitching. In an ideal situation with a solid object model, object size variations in the captured images may be implicitly taken care by the registration process. A corresponding object in different images can be identified and registered. The different object sizes in different images due to distance variations are presumably taken into consideration by the registration process. The object having a difference size in a target frame will be matched with the corresponding object in the reference frame. Likely, a global motion model will be applied to the target image to scale the object so that the image can be scaled and stitched properly. Nevertheless, the images associated with objects in the GI tract environment are usually far from the ideal solid object models. Furthermore, the iteration process may not always converge or converge to local minima when variables such as distance are involved in the optimization process. As is known in the field, the iteration process is usually used as part of the whole registration process. In one embodiment, the distance information is used for scaling. In particular, the distance information is used to assist the image registration to improve the registration accuracy.

FIG. 2A and FIG. 2B illustrate an example of the different sizes of object images for a same object in two images captured at two different object distances. In FIG. 2A, illustration 210 corresponds to the case that the capsule 211 is at a farther distance from an object of interest 213 of the GI tract 212. Image 220 corresponds to the image captured for illustration 210. In FIG. 2B, illustration 230 corresponds to the case that the capsule 211 is at a closer distance from an object of interest 213 of the GI tract 212. Image 240 corresponds to the image captured for illustration 230. Since image 240 is capture with the camera closer to the GI wall. Therefore, the object image in image 240 appears larger than the object image size in image 220. Therefore, the distance information can be used to scale the object in these two images.

In the GI tract environment, images are always captured using a light source to illuminate the field of view. When the camera is closer to an intestine wall, the object being imaged will be brighter and the image intensities will be higher. On the other hand, when the camera is farther from an intestine wall, the object being imaged will be dimmer and the image intensities will be lower. Therefore, the overall intensities of an image will depend on the distance between the object in the field of view and the camera. Since the object-camera distance is typically very short for the GI tract environment, the variation in the overall intensities of an image will be rather large. Such large intensity variation may degrade the registration performance and consequently lower the stitching performance.

Accordingly, in another embodiment of the present invention, the image intensities for two images to be registered will be adjusted according to the distance. The pixel intensities are roughly proportional to the distance square inversely or another functional form. The relation between the pixel intensities and the distance can also be tabulated instead of being represented in a functional form. The intensities of an image at a closer distance can be adjusted down to match with those of another image at a farther distance. Alternatively, the intensities of an image at a farther distance can be adjusted up to match with those of another image at a closer distance. After intensity adjustment to compensate the variation due to different distances, the registration and image stitching should perform better.

FIG. 3 illustrates an exemplary flowchart for capturing an image sequence along with structured-light images according to an embodiment of the present invention, where the distance information is derived from the structured-light images. The capsule device is administered to a patient in step 310. Non-structured light from a non-structured light source is projected to a scene in a field of view of the camera in step 320. Regular images formed on a common image plane of the camera are captured using the camera when the capsule device travels through a human gastrointestinal tract in step 330. Structured light from a structured light source is projected to the scene in the field of view of the camera in step 340. The structured-light images are captured using the camera when the capsule device travels through the human gastrointestinal tract in step 350, where the structured-light images are interleaved with regular images to derive distance information associated with objects in the regular images with respect to the camera. The structured-light images or derived information of the structured-light images is outputted in step 360. The distance information is outputted in step 370. The distance information extracted from structure light images implies that the respective distance information is determined at more than one point in the image or field of view. It's the intention of the present invention to include one or more points in image.

Figure 4:
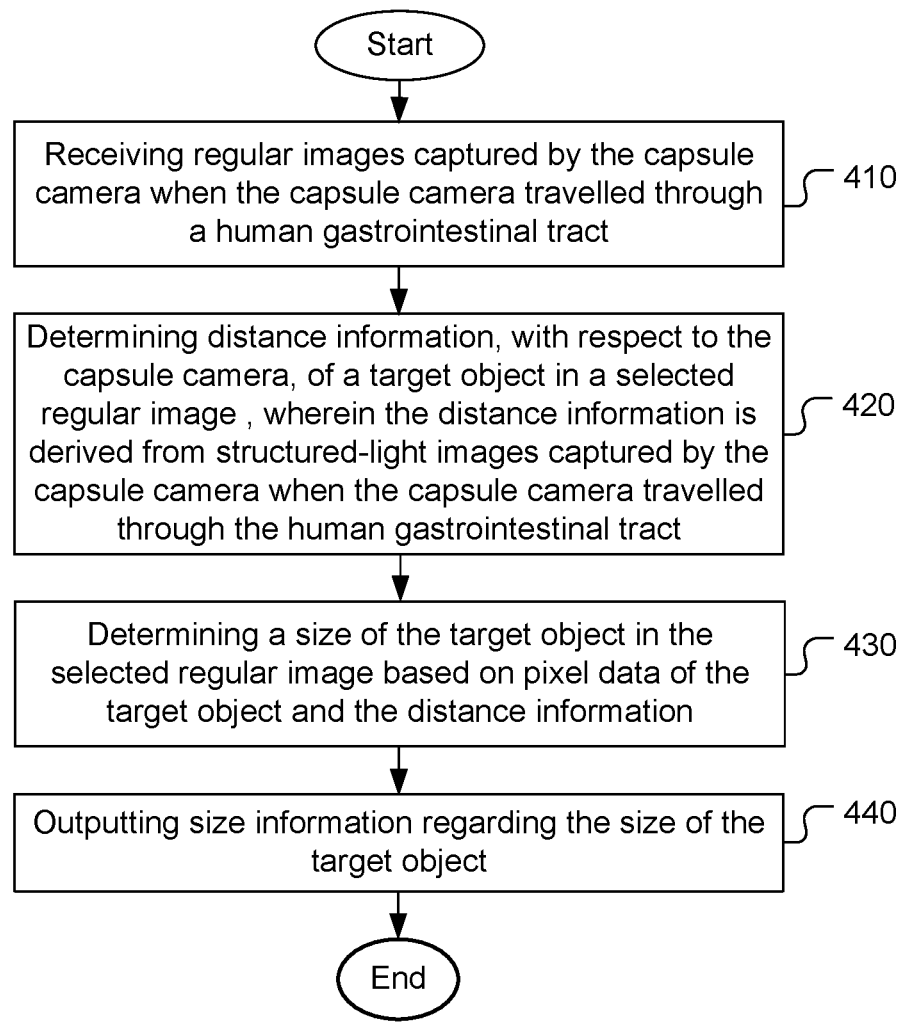
FIG. 4 illustrates an exemplary flowchart for determining a size of an object of interest in regular images based on pixel data of the object and the distance information according to an embodiment of the present invention.

FIG. 4 illustrates an exemplary flowchart for determining a size of an object of interest in the image sequence based on the image sequence and the distance information according to an embodiment of the present invention. Regular images captured by the capsule camera when the capsule camera traveled through a human gastrointestinal tract are received in step 410. The distance information, with respect to the capsule camera, associated with objects of a selected regular image is determined in step 420. The size of an object of interest in the selected regular image is determined based on pixel data of the target object and the distance information in step 430. The size information regarding the size of the object of interest is outputted in step 440.

Figure 5:
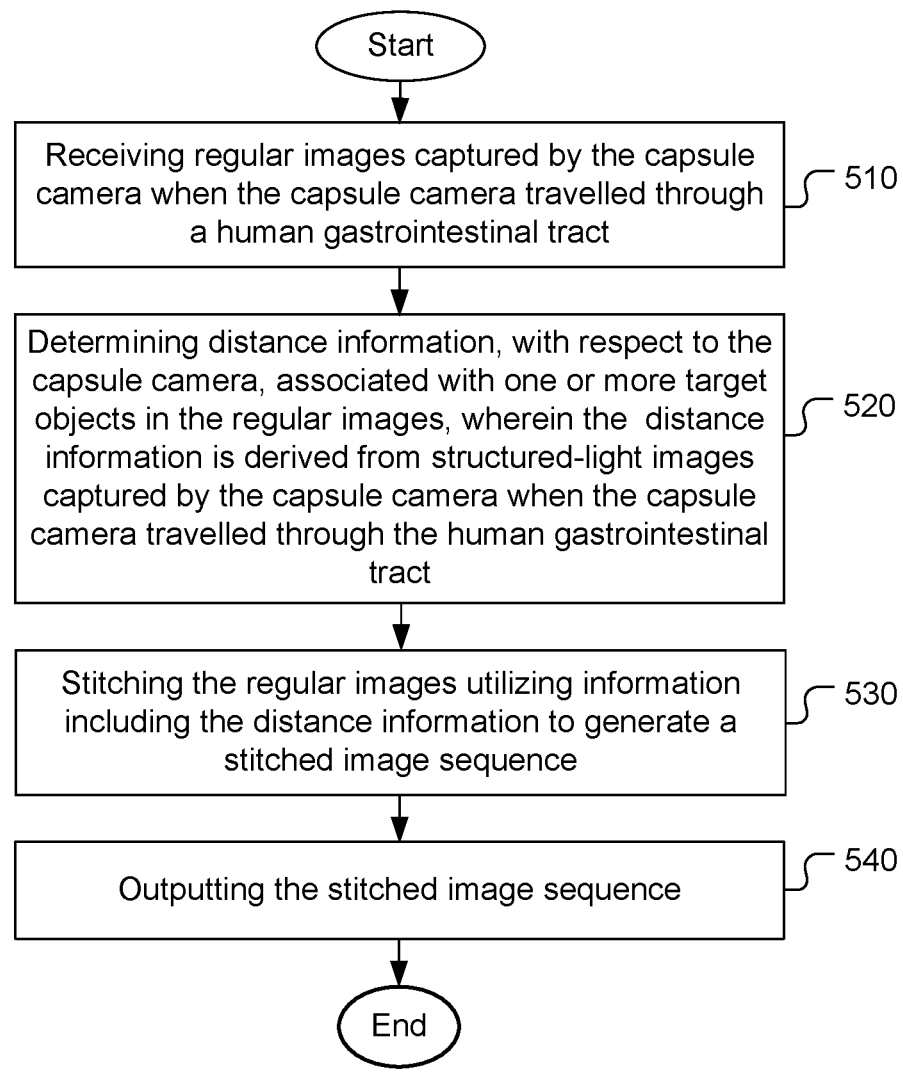
FIG. 5 illustrates an exemplary flowchart for stitching regular images utilizing information including the distance information to generate a stitched image sequence according to an embodiment of the present invention.

FIG. 5 illustrates an exemplary flowchart for stitching an image sequence utilizing information including the distance information to generate a stitched image sequence according to an embodiment of the present invention. Regular images captured by the capsule camera when the capsule camera traveled through a human gastrointestinal tract are received in step 510. The distance information with respect to the capsule camera associated with one or more objects in the regular images captured by the capsule camera when the capsule camera traveled through the human gastrointestinal tract is derived in step 520. The regular images are stitched utilizing information including the distance information to generate a stitched image sequence in step 530. The stitched image sequence is outputted in step 540.

The above description is presented to enable a person of ordinary skill in the art to practice the present invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method of capturing images of a scene using a capsule device including a camera, the method comprising:
administering the capsule device to a patient;
projecting non-structured light from a non-structured light source to a scene in a field of view of the camera;
capturing, by the camera, regular images formed on a common image plane of the camera when the capsule device travels through a human gastrointestinal tract;
projecting structured light from a structured light source to the scene in the field of view of the camera;
capturing, by the camera, structured-light images formed on the common image plane of the camera when the capsule device travels through the human gastrointestinal tract, wherein the structured-light images are interleaved with the regular images to derive distances associated with objects in the regular images with respect to the camera; and
outputting the regular images and
outputting the structured-light images for deriving information comprising the distances associated with the objects in the regular images based on the structured-light images or outputting derived information comprising the distances associated with the objects in the regular images, wherein each of the distances corresponds to one derived distance between one object in the regular image and the camera.

2. The method of claim 1 further comprises deriving the distances associated with the objects in the regular images based on the structured-light images.

3. The method of claim 2, wherein the derived information further comprises association information between the distances and corresponding images of the regular images.

4. The method of claim 3, wherein the association information corresponds to frame numbers or capture times of the corresponding images of the regular images.

5. An endoscope for capturing images of a scene using a capsule device, the capsule device comprising:
a camera;
a non-structured light source;
a structured light source;
one or more processors coupled to the camera and the structured light source;
one or more output interfaces coupled to said one or more processors; and
wherein said one or more processors are configured to:
capture regular images using the camera by projecting non-structured light from the non-structured light source when the capsule device travels through a human gastrointestinal tract;

capture structured-light images using the camera by projecting structured light from the structured light source to a scene in a field of view of the camera when the capsule device travels through the human gastrointestinal tract, wherein the structured-light images are interleaved with the regular images to derive distances associated with objects in the regular images with respect to the camera;

output the regular images through said one or more output interfaces; and output the structured-light images for deriving information comprising the distances associated with the objects in the regular images based on the structured-light images or outputting derived information comprising the distances associated with the objects in the regular images, wherein each of the distances corresponds to one derived distance between one object in the regular image and the camera; and a housing adapted to be swallowed, wherein the housing encloses the camera and said one or more processors in a sealed environment.

6. The capsule device of claim 5, wherein said one or more processors are configured further to derive the distances associated with the objects in the regular images based on the structured-light images.

7. The capsule device of claim 5, wherein the derived information further comprises association information between the distances and corresponding images of the regular images.

8. The capsule device of claim 7, wherein the association information corresponds to frame numbers or capture times of the corresponding images of the regular images.

9. A method of processing images captured using a capsule device including a camera, the method comprising:
receiving regular images captured by the camera when the capsule device traveled through a human gastrointestinal tract;
determining information comprising a distance associated with a target object in a selected regular image based on one or more structured-light images captured by the camera when the capsule device traveled through the human gastrointestinal tract, wherein the distance corresponds to one derived distance between the target object in the selected regular image and the camera;
determining a physical size of the target object in the selected regular image based on pixel data of the target object and the distance between the target object in the selected regular image and the camera; and
outputting size information regarding the physical size of the target object.

10. The method of claim 9, wherein the physical size of the target object is determined according to an image size of the target object in the selected regular image scaled by a ratio of distance associated with the target object to the camera and focal length of the camera.

11. The method of claim 10, wherein the image size of the target object is measured in terms of a number of pixels of the target object in the selected regular image.

12. The method of claim 9 further comprising receiving the structured-light images from the camera and deriving the distance associated with the target object in the regular images based on the structured-light images.

13. A method of processing images captured using a capsule device including a camera, the method comprising:
receiving regular images captured by the camera when the capsule device traveled through a human gastrointestinal tract;
determining information comprising a distance associated with a target object in a selected regular image based on one or more structured-light images captured by the camera when the capsule device traveled through the human gastrointestinal tract, wherein the distance corresponds to one derived distance between the target object in the selected regular image and the camera;
stitching the regular images utilizing the information including the distance to generate a stitched image sequence; and
outputting the stitched image sequence.

14. The method of claim 13 further comprising receiving the structured-light images from the camera and deriving the distance corresponding to one derived distance between the target object in the selected regular image and the camera based on the structured-light images.

15. The method of claim 14, wherein the distance is used to scale the target objects in the regular images for said stitching the regular images.

16. The method of claim 14, wherein the distance is used to adjust image intensities of at least one regular image for said stitching the regular images.

17. The method of claim 13, wherein association information between the distance and corresponding images of the regular images is also received and used for said stitching the regular images.

18. An apparatus for processing images captured using a capsule device including a camera, the apparatus comprising one or more electronic circuits or processors arranged to:
receive regular images captured by the camera when the device traveled through a human gastrointestinal tract;
determine information comprising a distance associated with a target object in a selected regular image based on one or more structured-light images captured by the camera when the capsule device traveled through the human gastrointestinal tract, wherein the distance corresponds to one derived distance between the target object in the selected regular image and the camera;
stitch the regular images utilizing the information including the distance to generate a stitched image sequence; and
output the stitched image sequence.

19. The apparatus of claim 18, wherein said one or more electronic circuits or processors are arranged further to receive the structured-light images from the camera and derive the distance corresponding to one derived distance between the target object in the selected regular image and the camera based on the structured-light images.

20. The apparatus of claim 18, wherein association information between the distance and corresponding images of the regular images is also received and used for stitching the regular images.

* * * * *

UNITED STATES PATENT AND TRADEMARK OFFICE
CERTIFICATE OF CORRECTION

PATENT NO.      : 10,402,992 B2
APPLICATION NO. : 15/883337
DATED           : September 3, 2019
INVENTOR(S)     : Kang-Huai Wang, Chenyu Wu and Yi Xu Page 1 of 1

It is certified that error appears in the above-identified patent and that said Letters Patent is hereby corrected as shown below:

On the Title Page

Item (63)/Related U.S. Application Data (Line 2), please insert:
--continuation-in-part of application No. 15/333,071, filed on Oct. 24, 2016, provisional application no. 62/268,975, filed on Dec. 17, 2015,-- after --PCT/US2017/015668, filed on Jan. 30, 2017,--

In the Specification

In CROSS REFERENCE TO RELATED APPLICATIONS section (Column 1, Line 10), please insert:
--The present invention is also a continuation-in-part application and claims priority to U.S. patent application Ser. No. 15/333,071, filed on Oct. 24, 2016, which is a nonprovisional application of and claims priority to U.S. provisional application, Ser. No. 62/268,975, filed on Dec. 17, 2015.-- after --US17/15668, filed on Jan. 30, 2017.--

Signed and Sealed this
Seventeenth Day of March, 2020

Andrei Iancu
*Director of the United States Patent and Trademark Office*